US00PP18687P2

(12) United States Plant Patent
Bradford

(10) Patent No.: US PP18,687 P2
(45) Date of Patent: Apr. 1, 2008

(54) INTERSPECIFIC TREE NAMED 'PLUMSWEET VI'

(50) Latin Name: ***Prunus* sp.**
Varietal Denomination: Plumsweet VI

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/634,860

(22) Filed: Dec. 7, 2006

(51) Int. Cl.
*A01H 5/00* (2006.01)

(52) U.S. Cl. ..... Plt./180
(58) Field of Classification Search ..... Plt./180
See application file for complete search history.

(56) References Cited

U.S. PATENT DOCUMENTS

PP15,809 P2 6/2005 Bradford

*Primary Examiner*—Kent Bell
*Assistant Examiner*—S. B. McCormick-Ewoldt

(57) ABSTRACT

The present invention relates to an interspecific tree and more particularly to a new and distinct variety broadly characterized by a large size, vigorous, hardy, and fairly productive tree. Being self-unfruitful, the present variety requires cross pollination from an apricot, plum, or interspecific that blooms during the early to mid season. The fruit matures under the ecological conditions described during mid June, with first picking on Jun. 20, 2006. The fruit is uniformly medium in size, mostly red with heavy greenish yellow freckling in skin color, clingstone in type, somewhat oblate in shape, red to pink in flesh color, very firm and crisp in texture, and excellent in flavor.

1 Drawing Sheet

Botanical classification: *Prunus* sp.
Varietal denomination: 'PLUMSWEET VI'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'PLUMSWEET VI'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2001 on such house container 'YUMMY®gem' (U.S. Plant Pat. No. 15,809) plum was crossed by me in this manner. To pollinate this plum I selected bouquets from several sources of apricot and interspecific plum-apricot hybrid trees without keeping specific written details. Upon reaching maturity the fruit from this plum tree was harvested and the seeds were removed, cracked, stratified and germinated as a group with the label "H10P881". They were grown as seedlings on their own root in my greenhouse and upon reaching dormancy transplanted to a cultivated area of my experimental orchard located near Le Grand, Calif. in Merced County (San Joaquin Valley). During the summer of 2004 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to 'YUMMY®gem' (U.S. Plant Pat. No. 15,809) plum by being self-unfruitful and by producing fruit that is sweet in flavor and clingstone in type, but is distinguished therefrom by producing fruit that is somewhat larger in size, that is oblate in shape, that is pink to red instead of yellow in flesh color, that has heavy greenish yellow freckling on the skin, and that matures about ten days later.

SUMMARY OF VARIETY

The present interspecific variety is characterized by a large size, vigorous, hardy, and fairly productive tree. Being self-unfruitful, the present variety requires cross pollination from an apricot, plum, or interspecific that blooms during the early to mid season. The present variety's abundance of blossoms and pollen entices strong bee activity to facilitate pollination. The fruit matures under the ecological conditions described during mid June, with first picking on Jun. 20, 2006. The fruit is uniformly medium in size, mostly red with heavy greenish yellow freckling in skin color, clingstone in type, somewhat oblate in shape, red to pink in flesh color, very firm and crisp in texture, and outstanding in flavor.

DRAWING

The accompanying photograph consists of four whole fruits positioned to display the characteristics of the skin color and form, one fruit divided transversely to the suture plane to reveal the flesh and stone, typical leaves, an inset depicting the blossoms as they appear on the tree, and tip shoot.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Jun. 24, 2006, on the original tree during its fifth growing season. The flower and bud descriptions were developed during the previous blooming season. All major color code designations are by reference to the Inter-Society Color Council, National Bureau of Standards. Common color names are also used occasionally.

Parentage:

*Seed parent.*—'YUMMY®gem' (U.S. Plant Pat. No. 15,809).

*Pollen parent.*—Unknown.

Tree

Size: Large, reaching and maintaining a height of 12' [3.66 m.] and a spread of 10' [3.05 m.] after five growing seasons utilizing typical dormant pruning.

Vigor: Strong, responding typically to irrigation and fertilization. The variety grows about 4' [1.22 m.] of surplus top-growth during the spring and summer. The plant should be grown on a standard commercial rootstock for production purposes.

Growth: Spreading and dense.

Form: Pruned to a perpendicular "v".

Hardiness: Hardy with respect to central California winters.

Head tolerance: Observed to perform adequately in typical central California climatic conditions, which typically include extended periods of heat.

Drought tolerance: Variety is developed for commercial orchards and requires regular irrigation.

Production: Fairly productive, thinning usually required.

Fertility: Self-unfruitful, requiring cross pollination by a suitable early blooming apricot, plum, or interspecific.

Bearing: Uncertain bearer, dependent upon favorable weather during the blooming period.

Trunk:

*Size.*—Large, reaching a maximum diameter of 6½" [165 mm.] after the fifth growing season.

*Texture.*—Shaggy.

*Bark color.*—A Dark grayish yellowish brown [81. d.gy.yBr] and Dark brown [59. d.Br] variegation with Light yellowish brown [76. l.yBr] crevices present.

*Lenticels.*—Approximate Number Per Square Inch: 9. Color: Deep orange yellow [69. deep OY]. Typical Size: 3/16" [4.8 mm.] to ½" [12.7 mm.]. Shape: Eye-shaped to elongated.

Branches:

*Size.*—Diameter of limb is 3" [76 mm.] measured 12" above the crotch, 2" [51 mm.] measured 12" above the first fork.

*Texture.*—Smooth on first and second year wood, increasing roughness with age.

*Color.*—1st Year Wood Topside: Light reddish brown [42. l.rBr]. 1st Year Wood Underside: Brilliant yellow green [116. brill.YG]. Older Wood: Light yellowish brown [76. l.yBr] with some Moderate olive [107. m.Ol] tinting showing through.

*Lenticels.*—Number Per square Inch: More than 50 on second year wood. Color: Moderate orange yellow [71. m.OY]. Typical size: 1/32" [0.8 mm.] to ⅛" [3.2 mm.]. Shape: Elongated.

Leaves:

*Size.*—Medium. Average Length: 3⅞" [98 mm.]. Average width: 1 15/16" [49 mm.].

*Arrangement.*—Alternate.

*Thickness.*—Medium.

*Form.*—Elliptical.

*Apex.*—Acuminate.

*Base.*—Mostly acute, with a base angle of 70 to 80 degrees, a few somewhat acuminate.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: ½" [12.7 mm.]. Average Thickness: 1/16" [1.6 mm.]. Color: Strong yellow green [117. s.YG].

*Stipules.*—Number: Usually 2 per leaf, up to 6 per growing tip. Average Length: ¼" [6.4 mm.]. Color: Brilliant yellow green [116. brill.YG] when young becoming Strong reddish brown [40. s.rBr] with maturity.

*Glands.*—Number: 0 to 4 observed, average 2. Position: Alternate, mostly on the petiole with some on the base of the blade. Size: Small. Form: Globose. Color: Strong yellow green [117. s.YG].

*Leaf buds.*—Medium, pointed.

Flower buds:

*Hardiness.*—Hardy, with respect to central California winters.

*Diameter.*—Typically 3/16" [4.8 mm.] 3 days before bloom.

*Length.*—Typically ⅜" [9.5 mm.] 3 days before bloom.

*Form.*—Not appressed.

*Surface.*—Pubescent.

*Color.*—White [263. White].

Flowers: Perfect, complete, perigynous, usually a single pistil, typically thirty or more stamens, five sepals and petal locations alternately positioned.

*Average flower diameter.*—15/16" [23.8 mm.].

*Number of petals.*—Five, no double blossoms observed.

*Petal shape.*—Oval to slightly obovate.

*Petal margin.*—Very wavy.

*Average petal diameter.*—5/16" [7.9 mm.].

*Average petal length.*—7/16" [11.1 mm.].

*Petal apex.*—Rounded.

*Petal base.*—Rounded to somewhat cuneate.

*Petal color.*—White [263. White].

*Anther color.*—Light yellow [86. l.Y].

*Stigma color.*—Pale greenish yellow [104. p.gY].

*Sepal color.*—Light yellow green [119. l.YG].

*Sepal length.*—5/32" [4.0 mm.].

*Sepal width.*—⅛" [3.2 mm.].

*Average pistil length.*—⅜" [9.5 mm.].

*Average stamens length.*—⅜" [9.5 mm.].

*Fragrance.*—Moderate.

*Pollen production.*—Abundant.

*Blooming period.*—Early to medium compared with other varieties.
*Onset of bloom.*—One percent on Feb. 17, 2006.
*Date of full bloom.*—Feb. 27, 2006.
*Duration of bloom.*—One to two weeks, dependent on ambient temperature.
*Number per cluster.*—2 to 10, average 5.

FRUIT

Maturity when described: Eating ripe, Jun. 24, 2006.
Date of first picking: Jun. 20, 2006.
Date of last picking: Jun. 30, 2006.
Size: Uniform, medium.
*Average diameter axially.*—2⅛" [54 mm.].
*Average diameter across cheek plane.*—2⅜" [60 mm.].
*Average diameter across suture plane.*—2⅜" [60 mm.].
*Typical weight.*—4.1 ounces [116 grams].
Form: Uniform, symmetrical, and oblate.
*Longitudinal section form.*—Elliptical to oblate.
*Transverse section through diameter.*—Circular.
Suture: an inconspicuous line from the apex to the shoulder, a shallow groove inside the stem cavity.
Ventral surface: Rounded.
Lips: Virtually no lips.
Cavity: Flaring, circular, suture showing on one side.
*Depth.*—⅜" [9.5 mm.].
*Breadth.*—1 1/16" [27.0 mm.].
Base: Truncate.
Apex: Rounded to slightly truncate.
Pistil point: An inconspicuous dot.
Stem: Medium.
*Average length.*—⅜" [9.5 mm.].
*Average width.*—⅛" [3.2 mm.].
Skin:
*Thickness.*—Medium.
*Surface.*—Smooth.
*Tenacity.*—Tenacious to flesh.
*Astringency.*—Moderate.
*Tendency to crack.*—None observed.
*Color.*—Very deep red [14. v.deep R] smoothly blending into Dark reddish orange [38. d.rO] background with heavy Dark greenish yellow [103. d.gY] freckling throughout.
*Bloom.*—Abundant.
Flesh:
*Color.*—A blend of Strong yellowish pink [26. s.yPk] with Dark red [16. d.R] streaking next to the skin and stone.
*Surface of pit cavity.*—Moderate reddish orange [37. m.rO] fibers breaking when twisted from stone.
*Amygdalin.*—Moderate.
*Juice.*—Abundant, rich.
*Texture.*—Firm and crisp.
*Fibers.*—Abundant, fine.
*Ripens.*—Slightly earlier toward the apex.
*Flavor.*—Mildly acidic and sweet, 17 to 20 brix.
*Aroma.*—Moderate.
*Eating quality.*—Very good.

STONE

Type. —Clingstone.
Form: Oval.
Hilum: Narrow, oblong.
Base: Straight.
Apex: Acuminate, with a 1/16" [1.6 mm] tip that has an angle of 40 to 50 degrees.
Sides: Equal.
Surface: Rough, with a single groove from the base to apex on each side of the dorsal fin.
External color of stone: Dark orange yellow [72. d.OY] when dried.
Pit wall color when cracked: Pale orange yellow [73. p.OY].
Cavity surface color: Light yellowish brown [76. l.yBr].
Average pit wall thickness: 1/16" [1.6 mm.].
Average width: ¾" [19.1 mm.].
Average length: ⅞" [22.2 mm.].
Average breadth: ⅜" [9.5 mm.].
Tendency to split: None observed.
Kernel:
*Form.*—Oval.
*Skin color.*—Light yellow [86. l.Y] when freshly removed.
*Pellicle color.*—Light yellowish brown [76. l.yBr.].
*Vein color.*—Strong yellowish brown [74. s.yBr].
*Taste.*—Very bitter.
*Viable.*—Yes.
*Average width.*—⅜" [9.5 mm.].
*Average length.*—9/16" [14.3 mm.].
*Amygdalin.*—Abundant.

Use

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusually susceptibilities noted.
Resistance to diseases: No unusual susceptibilities noted.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to 'YUMMYgem' (U.S. Plant Pat. No. 15,809) plum by being self-unfruitful and by producing fruit that is sweet in flavor and clingstone in type, but is distinguished therefrom by producing fruit that is somewhat larger in size, that is oblate in shape, that is pink to red instead of yellow in flesh color, that has heavy greenish yellow freckling on the skin, and that matures about ten days later.

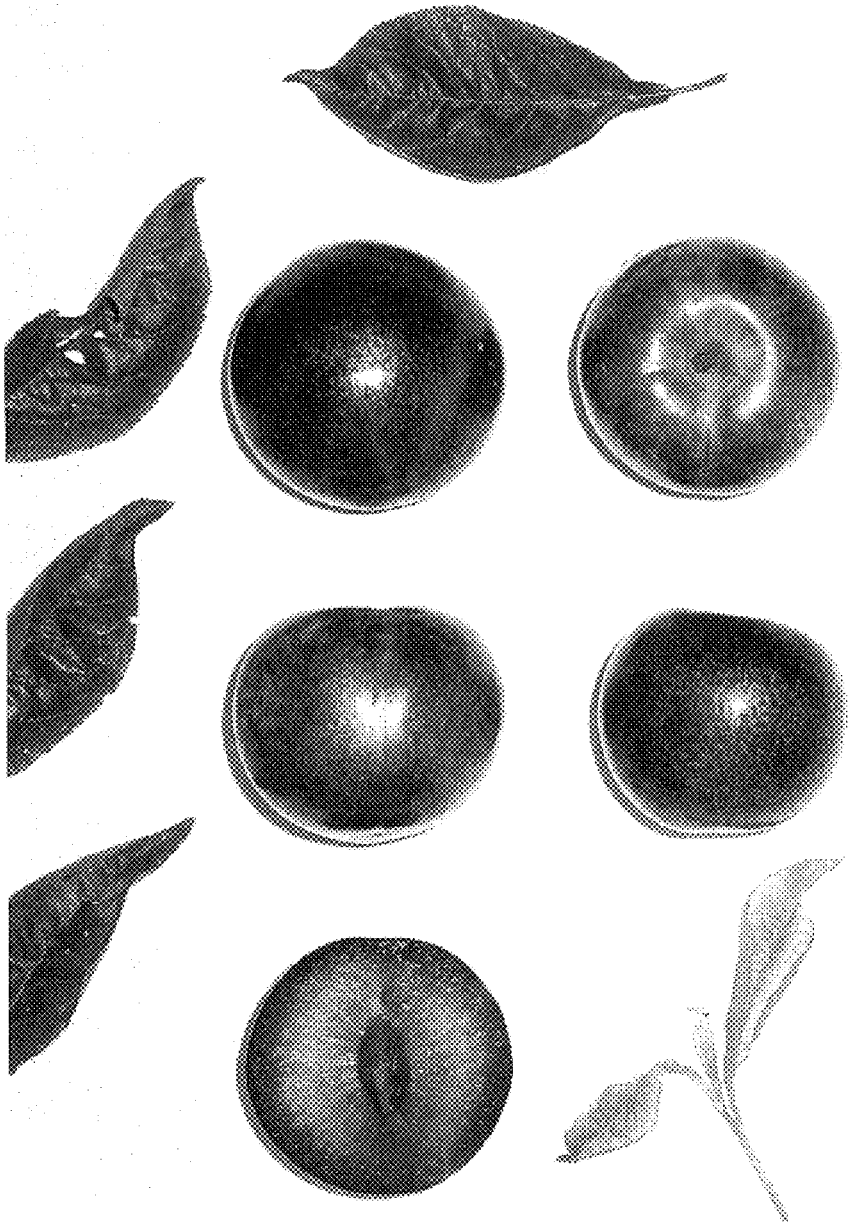
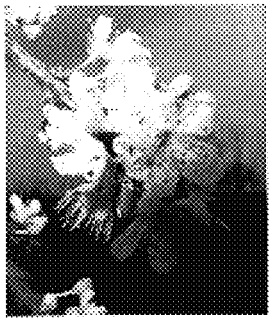

* * * * *